United States Patent [19]
Yamanaka et al.

[11] Patent Number: 5,418,137
[45] Date of Patent: May 23, 1995

[54] FLEA MEMBRANE BINDING SITE PROTEINS AS SCREENING TOOLS

[75] Inventors: Miles Yamanaka, Redwood City; Steve Reeves, San Francisco; Beverly Dale, Los Altos, all of Calif.

[73] Assignee: Paravax, Inc., Fort Collins, Colo.

[21] Appl. No.: 151,567

[22] Filed: Nov. 12, 1993

Related U.S. Application Data

[63] Continuation of Ser. No. 766,196, Sep. 26, 1991.

[51] Int. Cl.⁶ .................. C12Q 1/00; G01N 33/53
[52] U.S. Cl. ...................... 435/7.2; 435/7.1; 435/820; 530/858
[58] Field of Search .............. 435/7.1, 7.2, 820; 530/858

[56] References Cited

FOREIGN PATENT DOCUMENTS

WO88/03929  6/1988  WIPO .

OTHER PUBLICATIONS

Willadsen, P. et al (1989) J. Immunol. 143:1346–1351.
Morshedy, M. (1989) Alexandria Sci. Exch. 10:457–469.
Pincus, J. F. (1979) Diss. Abstr. Int. B 1980, 40(11),5115.
Takeyasu, K., et al., *J. Biol. Chem.* (1988) 263(9)4347–4354.
Takeyasu, K., et al., *J. Biol. Chem.* (1987) 262:10733–10740.
Lebovitz, R. M., et al., *Embro J.* (1989) 8:193–202.
Strosberg, A. D., et al., *Current Opinion in Biotechnology* (1991) 2:30–36.

*Primary Examiner*—Christine M. Nucker
*Assistant Examiner*—Julie Krsek-Staples
*Attorney, Agent, or Firm*—Morrison and Foerster

[57] ABSTRACT

The cellular binding proteins present in membranes of fleas, especially those which are present in the digestive tract, are useful as screening tools for systemic anti-flea reagents and in the design of vaccine formulations. Particularly useful is the $\alpha$-subunit of $(Na^+/K^+)$ATPase. The $\alpha$-subunit of this protein expressed in recombinant host cells in the presence of the $\beta$-subunit is distributed on the membrane and the recombinant cells can thus be used to screen candidates for ability to bind the cells. Secondary screens are used to determine the specificity of the candidate reagent for flea protein as compared to a corresponding protein derived from other sources.

3 Claims, 5 Drawing Sheets

```
243 /   1                                   273 /  11
ATG GAT GAT AAG CAT GGG CGT TCC GAT TCG TAT CGC GTG GCT ACA GTA CCT ACC ATA GAT
met asp asp lys his gly arg ser asp ser tyr arg val ala thr val pro thr ile asp
303 /  21                                   333 /  31
GAC AAT TTG ACA GCA GAC GGT CAA TAC AAG TCG CGA CGT AAA ACG CCA ACG AAA AAG CAA
asp asn leu thr ala asp gly gln tyr lys ser arg arg lys thr pro thr lys lys gln
363 /  41                                   393 /  51
AGG AAG GAA GGA GAG CTT GAT GAC TTG AAA CAA GAA TTA GAT ATC GAT TTT CAC AAA GTA
arg lys glu gly glu leu asp asp leu lys gln glu leu asp ile asp phe his lys val
423 /  61                                   453 /  71
TCA CCC GAA GAA TTA TAT CAA CGA TTT AAT ACT CAC CCC GAA AAT GGT CTT AGT CAC GCC
ser pro glu glu leu tyr gln arg phe asn thr his pro glu asn gly leu ser his ala
483 /  81                                   513 /  91
AAG GCG AAA GAA AAC TTA GAA AGA GAT GGA CCG AAT GCT TTG ACC CCG CCG AAA CAA ACA
lys ala lys glu asn leu glu arg asp gly pro asn ala leu thr pro pro lys gln thr
543 / 101                                   573 / 111
CCA GAA TGG GTC AAA TTT TGC AAG AAC TTG TTT GGA GGA TTC GCC TTG TTG TTG TGG ATC
pro glu trp val lys phe cys lys asn leu phe gly gly phe ala leu leu leu trp ile
603 / 121                                   633 / 131
GGT GCC ATT TTA TGT TTT GTC GCA TAC TCC ATC CAA GCT AGT ACT GTG GAA GAA CCA GCA
gly ala ile leu cys phe val ala tyr ser ile gln ala ser thr val glu glu pro ala
663 / 141                                   693 / 151
GAT GAT AAT TTG TAT CTT GGT ATT GTA TTG GCG GCT GTA GTT ATA GTT ACT GGT ATA TTT
asp asp asn leu tyr leu gly ile val leu ala ala val val ile val thr gly ile phe
723 / 161                                   753 / 171
TCG TAT TAC CAA GAA TCC AAG AGT TCC AAA ATT ATG GAA AGT TTC AAA AAC ATG GTT CCA
ser tyr tyr gln glu ser lys ser ser lys ile met glu ser phe lys asn met val pro
783 / 181                                   813 / 191
CAG TTT GCA ACA GTA TTA CGT GAA GGT GAA AAA TTA ACC TTA CGA GCG GAA GAT TTA GTA
gln phe ala thr val leu arg glu gly glu lys leu thr leu arg ala glu asp leu val
843 / 201                                   873 / 211
CTC GGA GAT GTC GTA GAA GTG AAA TTC GGC AGC AGG ATA CCT GCA GAT ATC CGT ATT ATT
leu gly asp val val glu val lys phe gly ser arg ile pro ala asp ile arg ile ile
903 / 221                                   933 / 231
GAA AGC CGA GGA TTC AAG GTA GAC AAG TCT TCC TTG ACT GGT GAA TCA GAA CCT CAA TCT
glu ser arg gly phe lys val asp lys ser ser leu thr gly glu ser glu pro gln ser
963 / 241                                   993 / 251
CGA GGT CCC GAG TTT ACA AAT GAA AAG CCT TTA GAA ACG AAG AAC TTG GCG TTC TTC TCT
arg gly pro glu phe thr asn glu lys pro leu glu thr lys asn leu ala phe phe ser
1023 / 261                                  1053 / 271
ATC AAC GCC GTC GAA GGT ACT GCC AAA GGT GTC GTT ATC AGC TGT GGA GAC AAC ACT GTC
ile asn ala val glu gly thr ala lys gly val val ile ser cys gly asp asn thr val
1083 / 281                                  1113 / 291
ATG GGT CGT ATT GCC GGC TTG GCT TCA GGC TTG GAC ACT GGG GAG ACT CCA ATC GCT AAA
met gly arg ile ala gly leu ala ser gly leu asp thr gly glu thr pro ile ala lys
1143 / 301                                  1173 / 311
GAA ATT CAT CAC TTC ATT CAT CTC ATC ACT GGA GTC GCT GTA TTT TTA GGT GTA ACA TTC
glu ile his his phe ile his leu ile thr gly val ala val phe leu gly val thr phe
1203 / 321                                  1233 / 331
TTT GTT ATT GCA ATT ATT TTG AAC TAC CAT TGG TTA GAC GCT GTC ATC TTC TTG ATT GGT
phe val ile ala ile ile leu asn tyr his trp leu asp ala val ile phe leu ile gly
1263 / 341                                  1293 / 351
ATC ATC GTC GCT AAT GTC CCT GAA GGT TTA TTG GCT ACT GTA ACC GTA TGT CTA ACC CTT
ile ile val ala asn val pro glu gly leu leu ala thr val thr val cys leu thr leu
```

FIG. 2A

```
1323 /  361
ACT GCT AAG CGT ATG GCA TCC AAG AAT TGT CTT GTC AAG AAT CTT GAA GCT GTA GAA ACT
thr ala lys arg met ala ser lys asn cys leu val lys asn leu glu ala val glu thr
1383 /  381                                 1413 /  391
CTT GGT TCT ACC TCA ACT ATC TGC TCA GAC AAA ACT GGC ACA CTG ACC CAG AAC AGA ATG
leu gly ser thr ser thr ile cys ser asp lys thr gly thr leu thr gln asn arg met
1443 /  401                                 1473 /  411
ACT GTA GCC CAC ATG TGG TTT GAC AAC CAG ATT ATT GAA GCC GAC ACC ACT GAA GAT CAA
thr val ala his met trp phe asp asn gln ile ile glu ala asp thr thr glu asp gln
1503 /  421                                 1533 /  431
TCT GGA GTC GTA TAT GAC AGA ACC AGC CCT GGT TTC AAA GCT TTG GCG CGC ATT GCA ACT
ser gly val val tyr asp arg thr ser pro gly phe lys ala leu ala arg ile ala thr
1563 /  441                                 1593 /  451
TTG TGC AAC AGA GCA GAA TTC AAG GGA GGT CAG GAA GGT GTA CCC ATC TTG AAA AAA GAA
leu cys asn arg ala glu phe lys gly gly gln glu gly val pro ile leu lys lys glu
1623 /  461                                 1653 /  471
GTC AGT GGT GAT GCA TCT GAA GCT GCT CTT CTC AAA TGT ATG GAA CTG GCT TTA GGA GAT
val ser gly asp ala ser glu ala ala leu leu lys cys met glu leu ala leu gly asp
1683 /  481                                 1713 /  491
GTT ATG TCT ATT CGA AAA CGA AAT AAG AAA GTC TGT GAA ATT CCA TTT AAC TCC ACA AAC
val met ser ile arg lys arg asn lys lys val cys glu ile pro phe asn ser thr asn
1743 /  501                                 1773 /  511
AAA TAC CAG GTT TCC ATT CAC GAA ACT GAA GAT GCG TCA GAC CCC CGT CAT GTA ATG GTT
lys tyr gln val ser ile his glu thr glu asp ala ser asp pro arg his val met val
1803 /  521                                 1833 /  531
ATG AAA GGA GCT CCT GAA AGA ATC TTA GAA AAA TGT TCC ACC ATC TTC ATT GGA GGA AAG
met lys gly ala pro glu arg ile leu glu lys cys ser thr ile phe ile gly gly lys
1863 /  541                                 1893 /  551
GAA AAA CTA CTG GAC GAA GAG ATG AAA GAA GCT TTC AAT AAT GCA TAT CTG GAA TTG GGC
glu lys leu leu asp glu glu met lys glu ala phe asn asn ala tyr leu glu leu gly
1923 /  561                                 1953 /  571
GGT CTT GGA GAG CGT GTA TTG GGC TTT TGT GAT CTC ATG TTG CCT ACA GAC AAA TTC CCC
gly leu gly glu arg val leu gly phe cys asp leu met leu pro thr asp lys phe pro
1983 /  581                                 2013 /  591
TTA GGT TTC AAA TTC GAC AGC GAT GAT CCC AAC TTC CCA ATT GAA AAC CTT AGA TTT GTT
leu gly phe lys phe asp ser asp asp pro asn phe pro ile glu asn leu arg phe val
2043 /  601                                 2073 /  611
GGA CTC ATG TCT ATG ATT GAT CCT CCT AGA GCT GCC GTA CCT GAC GCT GTT GCC AAG TGC
gly leu met ser met ile asp pro pro arg ala ala val pro asp ala val ala lys cys
2103 /  621                                 2133 /  631
CGA TCT GCT GGT ATC AAG GTT ATC ATG GTT ACA GGA GAT CAT CCA ATC ACT GCA AAA GCC
arg ser ala gly ile lys val ile met val thr gly asp his pro ile thr ala lys ala
2163 /  641                                 2193 /  651
ATT GCT AAA TCA GTG GGT ATC ATC TCA GAG GGT AAT GAA ACT GTA GAA GAT ATC GCG CAA
ile ala lys ser val gly ile ile ser glu gly asn glu thr val glu asp ile ala gln
2223 /  661                                 2253 /  671
AGA TTG AAT ATT CCT GTA TCA GAG GTA AAT CCA CGA GAA GCC AAG GCA GCT GTT GTA CAT
arg leu asn ile pro val ser glu val asn pro arg glu ala lys ala ala val val his
2283 /  681                                 2313 /  691
GGA ACT GAG CTT AGG GAA CTC AAC TCT GAT CAG CTC GAT GAA ATT CTT AGG TAT CAC ACT
gly thr glu leu arg glu leu asn ser asp gln leu asp glu ile leu arg tyr his thr
2343 /  701                                 2373 /  711
GAA ATT GTA TTT GCT CGG ACA TCT CCT CAA CAA AAG CTG ATT ATT GTT GAA GGA TGC CAA
glu ile val phe ala arg thr ser pro gln gln lys leu ile ile val glu gly cys gln
```

FIG. 2B

```
2403 /  721                                          2433 /  731
CGT ATG GGT GCT ATT GTC GCC GTA ACT GGT GAT GGT GTG AAT GAC TCA CCT GCT TTG AAA
arg met gly ala ile val ala val thr gly asp gly val asn asp ser pro ala leu lys
2463 /  741                                          2493 /  751
AAG GCT GAT ATT GGT GTT GCC ATG GGT ATT GCC GGA TCT GAT GTA TCA AAA CAG GCT GCT
lys ala asp ile gly val ala met gly ile ala gly ser asp val ser lys gln ala ala
2523 /  761                                          2553 /  771
GAC ATG ATT TTA TTA GAT GAC AAC TTT GCA TCT ATT GTC ACT GGT GTG GAA GAG GGT CGT
asp met ile leu leu asp asp asn phe ala ser ile val thr gly val glu glu gly arg
2583 /  781                                          2613 /  791
TTG ATA TTC GAC AAT GCT AAG AAA TCT ATT GCT TAC ACA TTG ACT TCA AAT ATC CCA GAA
leu ile phe asp asn leu lys lys ser ile ala tyr thr leu thr ser asn ile pro glu
2643 /  801                                          2673 /  811
ATT TCA CCA TTC TTG GCA TTC ATC TTA TGT GAT ATC CCG CTA CCT TTG GGA ACT GTA ACA
ile ser pro phe leu ala phe ile leu cys asp ile pro leu pro leu gly thr val thr
2703 /  821                                          2733 /  831
ATC TTG TGC ATT GAC TTG GGA ACT GAC ATG GTG CCT GCC ATC TCA TTG GCC TAC GAA CAT
ile leu cys ile asp leu gly thr asp met val pro ala ile ser leu ala tyr glu his
2763 /  841                                          2793 /  851
GCT GAA GCT GAT ATC ATG AAG AGG CCG CCT AGA GAT CCA GTC AAT GAC AAA CTT GTA AAT
ala glu ala asp ile met lys arg pro pro arg asp pro val asn asp lys leu val asn
2823 /  861                                          2853 /  871
TCC AGA CTT ATC TCT ATG GCT TAT GGG CAA ATC GGA ATG ATT CAA GCA GCT GCT GGA TTC
ser arg leu ile ser met ala tyr gly gln ile gly met ile gln ala ala ala gly phe
2883 /  881                                          2913 /  891
TTT GTA TAC TTT GTA ATC ATG GCT GAA AAT GGA TTC TTA CCC ATG AAA TTG TTT GGA ATT
phe val tyr phe val ile met ala glu asn gly phe leu pro met lys leu phe gly ile
2943 /  901                                          2973 /  911
AGA AAA CAA TGG GAC TCG AAA GCT GTC AAT GAT CTA ACA GAT TCT TAT GGA CAA GAA TGG
arg lys gln trp asp ser lys ala val asn asp leu thr asp ser tyr gly gln glu trp
3003 /  921                                          3033 /  931
ACA TAC AGA GAT CGC AAG ACT CTT GAA TAT ACC TGC CAC ACT GCC TTC TTC GTC TCT ATT
thr tyr arg asp arg lys thr leu glu tyr thr cys his thr ala phe phe val ser ile
3063 /  941                                          3093 /  951
GTC GTT GTA CAA TGG GCT GAT TTG ATT GTC TGC AAA ACG CGC CGT AAT TCC TTG TTA CAC
val val val gln trp ala asp leu ile val cys lys thr arg arg asn ser leu leu his
3123 /  961                                          3153 /  971
CAG GGA ATG AGA AAT TGG GCT CTC AAC TTT GGT CTA GTT TTT GAA ACT GCC TTA GCA GCA
gln gly met arg asn trp ala leu asn phe gly leu val phe glu thr ala leu ala ala
3183 /  981                                          3213 /  991
TTC CTG TCA TAC ACA CCA GGA ATG GAC AAG GGA CTG AGG ATG TTC CCA CTG AAG TTT GTT
phe leu ser tyr thr pro gly met asp lys gly leu arg met phe pro leu lys phe val
3243 / 1001                                          3273 / 1011
TGG TGG CTG CCT GCT CTG CCA TTC ATG ATT TCC ATC TTC ATC TAT GAT GAG ACT AGA AGA
trp trp leu pro ala leu pro phe met ile ser ile phe ile tyr asp glu thr arg arg
3303 / 1021                                          3333 / 1031
TTT TAC CTA CGT CGC AAC CCT GGT GGT TGG TTA GAA CAA GAA ACA TAT TAT
phe tyr leu arg arg asn pro gly gly trp leu glu gln glu thr tyr tyr
```

FIG. 2C

FLEA MEMBRANE BINDING SITE PROTEINS AS SCREENING TOOLS

This application is a continuation of application Ser. No. 07/766,196, filed 26 Sep. 1991.

TECHNICAL FIELD

The invention relates to amelioration of flea infestation. In particular, it concerns a class of flea midgut membrane binding site moieties which provide an assay method for systemic agents that diminish flea infestation and that provide the basis for vaccine formulation.

BACKGROUND ART

The control of flea parasites on small and large animals is not a solved problem. The presently known agents to target the flea population that infests these hosts are generally poisons that target the nervous system, such as organophosphates. These agents are notably toxic to the host as well. Accordingly, controlled doses of systemics must be used, and they are less than totally effective.

On the other hand, reagents which target flea membrane binding sites, especially those which inhabit the digestive tract, can be designed to be more flea specific. In addition, those membrane binding sites which are present in the flea midgut can provide a mechanism for direct administration to the flea through the ingestion of the blood meal.

Systemic agents against ticks, which, unlike fleas, are not insects, have been proposed where the target is the plasma membrane of the gut cells. PCT application WO 88/03929 to Biotechnology Australia et al. describes an antigen derived from a tick species or cell line that produces an immune response capable of damaging the plasma membrane of gut cells. The applicants claim that the damage is so extensive that the majority of ticks fail to survive to adult stage.

One important cell membrane receptor protein is the dimer associated with $Na^+$ and $K^+$ transfer across the cell membrane-$(Na^+/K^+)$ATPase or the "sodium pump." This protein has been studied in a number of species and the genes have been cloned. Sequencing of the genes for both $\alpha$ and $\beta$ subunits shows a high degree of homology in mammalian, avian, fish, and insect (*Drosophila*) species. The $\alpha$-subunit of the dimer is considered to be the catalytic subunit, but it appears that the $\beta$-subunit may be required to position the catalytic subunit at the cell's surface.

Takeyasu, K., et al., *J Biol Chem* (1988) 263:4347–4354, catalog the literature relating to the retrieval of cDNAs encoding the $\alpha$-subunits of piscine and mammalian sodium pumps and the $\beta$-subunits of piscine, avian and mammalian pumps. This article presents information concerning the avian $\alpha$-subunit which is expressed in mouse L-cells. The recombinant cells that expressed the avian $\alpha$-subunits displayed high-affinity ouabain binding (ouabain is known to bind the sodium pump) and ouabain-sensitive rubidium uptake (rubidium uptake is a diagnostic for the function of the sodium pump). However, fluorescence labeling shows that mouse L-cells expressing the gene for the $\alpha$ subunit of the $(Na^+/K^+)$ATPase produced the majority of the protein internal to the cells, in contrast to the almost exclusively surface distribution of the $\beta$-subunit expressed in these cells (Takeyasu, K., et al., *J Biol Chem* (1987) 262:10733–10740).

This work was extended to *Drosophila* pump by the same group and described in an article by Lebovitz, R. M., et al., *Embo J* (1989) 8:193-102. These authors found ouabain-sensitive rubidium uptake in tissue cultures of *Drosophila* cells and cross-reactivity for a monoclonal antibody to the avian sodium pump $\alpha$-subunit with the *Drosophila* pump $\alpha$-subunit. The distribution in *Drosophila* tissues was studied by immunofluorescence microscopy and high levels of the protein were detected in the malpighian tubules, in direct flight muscles, in tubular muscles, and throughout the nervous system. The cDNA encoding the $\alpha$-subunit was cloned and found to be 80% homologous to the $\alpha$-subunit sequences of vertebrates. The $\alpha$-subunit gene was also expressed in mouse L-cells.

The use of receptor proteins in assay systems which can be used to screen for ligands binding to such receptors has been reviewed by Strosberg, A. D., et al., in *Current Opinion in Biotechnology* (1991) 2:30–36. A number of formats are described which permit the use of such receptors in assays, including the expression of recombinantly-produced receptors at the surfaces of host cells. This review includes a discussion of the use of bacterial cells as hosts to provide the receptors for such screens.

The present invention is directed to flea midgut membrane cellular binding site proteins, specifically provided in recombinant form, to screen for anti-flea systemic reagents and to provide the basis for vaccine formulations.

DISCLOSURE OF THE INVENTION

The binding site proteins present in membranes of fleas, especially those which are present in the digestive tract, are useful as screening tools for systemic anti-flea reagents and in the design of vaccine formulations. Particularly useful is the $\alpha$-subunit of $(Na^+/K^+)$ATPase. The $\alpha$-subunit of this protein expressed in recombinant host cells in the presence of the $\beta$-subunit is distributed on the membrane and the recombinant cells can thus be used to screen candidates for ability to bind the cells. Secondary screens are used to determine the specificity of the candidate reagent for flea protein as compared to a corresponding protein derived from other sources. In addition, the extracellular regions provide peptide-based vaccines for immunization of subject hosts.

Thus, in one aspect, the invention is directed to methods to screen for reagents which are useful in the control of flea infestation, which method comprises contacting flea midgut membrane cellular binding protein recombinantly produced in the membrane of a host cell with a candidate reagent and determining the degree of binding of the candidate reagent to the cells. In a second aspect, the invention relates to use of this method wherein the method further includes comparing the ability of the candidate reagent to bind the recombinantly-expressed flea membrane protein to its ability to bind comparable membrane proteins of other species, in particular the host species. In a third aspect, the invention is directed to peptide-based vaccines wherein the peptides have amino acid sequences which correspond to at least one extracellular region of a flea membrane cellular binding site protein.

BRIEF DESCRIPTION OF THE DRAWINGS

FIGS. 2A, 2B and 2C shows the nucleotide sequence of α-subunit of flea Na+ pump (SEQ ID NO:12) and (SEQ ID NO:13).

MODES OF CARRYING OUT THE INVENTION

Figure 1:
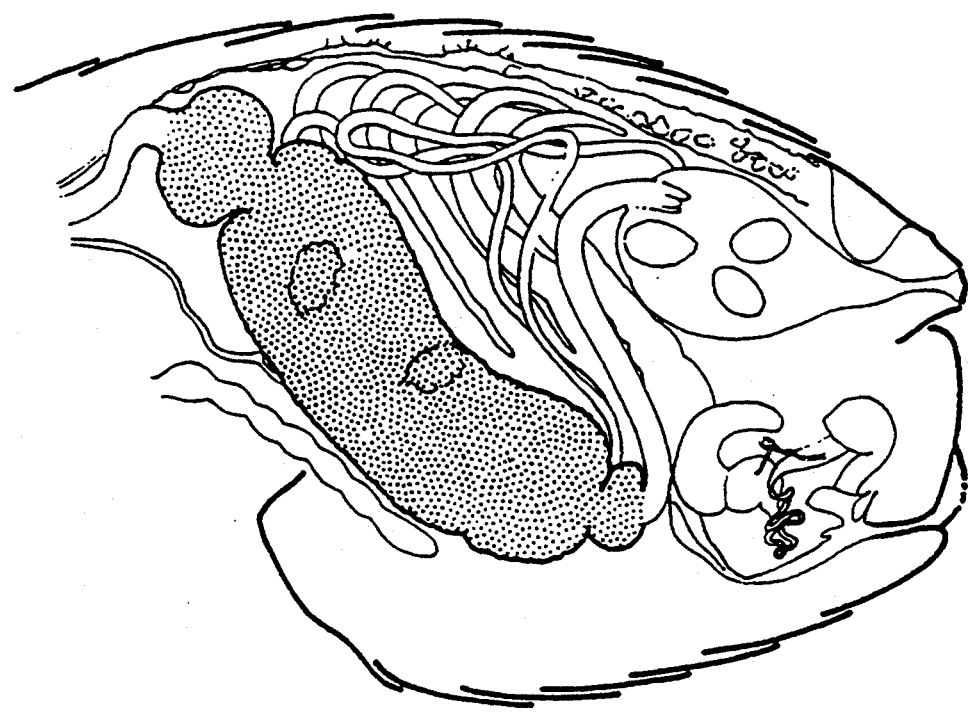
FIG. 1 shows a diagram which indicates the localization of flea Na+/K+ ATPase sodium pump in the midgut.

The invention provides screening methods and vaccines for use in the control of flea infestation. The screens and the vaccines employ recombinantly produced proteins that represent the cellular binding sites present in the flea midgut. Among the useful flea membrane binding site proteins is the (Na+/K+)ATPase sodium pump. Additional proteins that constitute cellular binding sites in the flea midgut are detected and characterized utilizing the PCR reaction with respect to a flea midgut cDNA library. The published DNA sequences encoding any receptor or other cellular binding site of vertebrates or invertebrates may be used for the design of primers, and the amplified cDNA from the flea midgut library sequenced. In addition, antisera raised in experimental animals against flea midgut membranes or monoclonals prepared from these immunized animals may be used to localize cellular receptor binding sites. Particular localization of such binding sites may be characteristic for such sites in general, as shown in FIG. 1, which indicates the specific location of the Na+/K+ATPase sodium pump in the flea midgut. The efficacy of such approaches is further illustrated using the sodium pump as typical is set forth in the examples hereinbelow.

Methods for Screening Candidate Reagents

The genes encoding the various membrane binding site proteins are cloned and expressed in suitable host cells capable of disposing the catalytic or diagnostic portion of the protein at the cell membrane. Suitable host cells include those which are capable of this processing, and include procaryotic and eucaryotic hosts. Suitable procaryotic hosts include, most prominently, $E.\ coli$, although other bacterial species, such as $Bacillus$, could also be used. Eucaryotes include yeast, fungi, mammalian cells, insect cells, and even cells of higher plants. The genes encoding the binding site protein are ligated into expression systems so as to be operably linked to control sequences compatible with the host which effect the expression of the encoding portion of the gene. The control sequences can effect either constitutive or inducible expression and are designed for the desired level of efficiency.

Particularly favored recombinant expression is in mammalian cells and the coding region of the cDNA or genomic DNA encoding the flea membrane protein is then ligated into standard mammalian expression vectors, for example, downstream of the human β-actin promoter present in LK444 (Gunning, P., et al., $Proc\ Natl\ Acad\ Sci\ USA$ (1987) 84:5831–5835) or regulated expression may be obtained using a commercially available system such as the pMAM vector of Clonetech Laboratories, Inc. pMAM contains the murine mammary tumor virus promoter, that is regulatable with dexamethasone. The host cells, such as CHO, mouse L-cells, are transformed using standard protocols such as lipofection, electroporation or calcium phosphate-mediated transfection. Stable cell lines are selected using standard G418 selection or other selection schemes depending on the markers used.

Expression systems for sodium pump encoding DNA have also been demonstrated in yeast by Horowitz, B., et al., $J\ Biol\ Chem$ (1990) 265:4189–4192. In the yeast system, both the α- and β-subunit of the sodium pump are necessary for active expression, and commercially available vectors such as the pYES1 vector from Invitrogen can be used as host expression systems. Stable yeast transformants are obtained by standard transfection techniques using spheroplast transformation and plating on Selective medium. For the use of pYES1, the host cells are of the ura3 phenotype and the selective medium is synthetic complete medium minus uracil.

The foregoing are merely illustrative; techniques for effecting expression of foreign genes in recombinant hosts are by now well known in the art.

The production of the membrane binding site protein at the membrane of the host cell permits the use of the host cell as the critical component of an assay system for screening candidate reagents for control of flea infestation. By "reagent" for the control of flea infestation is meant a substance that is capable of interrupting the course of infestation by these insects by virtue of its ingestion by the flea during its ingestion of a blood meal. Thus, these reagents will be passed directly from the bloodstream of the host to the digestive system of the flea.

In a primary screen for successful candidate reagents, the candidate is contacted with the recombinant host cell displaying the flea membrane binding site at its surface and the degree of binding of the reagent to the receptor is assessed. Quantitative assessment of the degree of binding is not necessarily required, and a qualitative conclusion that the candidate reagent binds well will suffice. The nature of the method to assess the degree of binding may depend on the nature of the binding site protein or may generically comprise, for example, the ability of the reagent to inhibit the binding of binding site protein-specific antibody.

Thus, in one approach, antibodies are prepared to recombinantly-produced or natively-isolated flea membrane binding site protein using standard immunization protocols in mammalian hosts, and measuring antibody titers to verify successful antibody production. Polyclonal antisera could be used, but preferably antibody-secreting cells such as spleen cells are immortalized and screened against the protein binding site antigen to obtain monoclonal preparations.

In a general assay method workable for any flea membrane binding site, the ability of the resulting antibodies to complex to cells expressing the membrane protein will be inhibited by successful candidate reagents. A variety of protocols can be formulated, but perhaps the most direct is to provide labeled antibody and detect the diminution of label uptake in the presence of the candidate reagent.

In addition to competitive binding assays, membrane cellular binding site proteins which mediate enzymatic or physiological effects permit assessment for agonist candidate reagents through measuring the enhancement of activity in the presence of these reagents, or for antagonist candidate reagents by virtue of their ability to block the activities of controls. For example, growth factor receptors become active kinases following ligand binding and catalyze the phosphorylation of tyrosine residues contained in protein. Similarly, the sodium ion pump effects the ion flux inside and outside the cell. The effect of the candidate reagent either as an antagonist or agonist on such activities is a measure of its ability to bind.

The successful candidates should then be subjected to a secondary screen to determine their specificity for flea protein as compared to protein corresponding to the membrane binding site produced in the host species. This can be done by a direct comparison of the ability of the candidate to bind to the flea membrane protein recombinantly expressed as compared to cells expressing the membrane protein corresponding to that in the flea that is characteristic of the recombinant host. In this secondary screen, assessment of agonist or antagonist activity is preferred, since use of antibodies specifically reactive with the flea membrane protein may be inappropriate as comparison reagents with respect to the host corresponding protein. Alternatively, if cells comparable to those of the native flea host are used as the recombinant host cells, comparison can be made to background binding of untransfected cells.

Typically, the techniques for determining the capacity of candidate reagents to bind to flea membrane cellular binding site proteins corresponding to those of the flea in other species is conducted as described above, but substituting either recombinantly produced corresponding membrane proteins or the membrane proteins as they reside on native cell surfaces. By "corresponding" receptor protein is meant that protein in the other species that represents the same function as, and is evolutionarily related to, the flea membrane protein studied. Thus, the "corresponding protein" to (Na+/K+)ATPase would be the (Na+/K+)ATPase found in dogs, cats, or closely related mammalian species.

Final confirmation of the efficacy of the potential anti-flea reagent is made using standard procedures to verify effects on the native membrane binding site protein and its toxicity levels in the intended host. For example, for the sodium pump, the effects of the candidate pesticide reagent on ouabain-inhibitable ATPase activity in whole flea or midgut membrane preparations is measured and compared to the effects on ouabain-inhibitable ATPase activity in dog or cat membrane preparations from various organs. In addition, the ability of the pesticide reagent to kill fleas using an in vivo assay which employs an artificial apparatus to introduce the candidate pesticide into the flea is conducted as a confirmatory test.

Pesticide Compositions

The successful candidate pesticide reagents are then formulated for administration to the host using standard formulations generally known in the art for administration of anti-flea pesticides. These formulations are designed for oral or topical delivery to the host or may be injected. Typically, the active ingredient is formulated in inert carriers suitable for the mode of administration. Dosage levels and concentrations are adjusted according to the results of the assay systems described in the section above.

Vaccines

The flea cellular membrane binding proteins can be sequence-analyzed using known techniques to find regions of hydrophobicity which presumably are embedded in the membrane and are thus transitions between intracellular and extracellular regions of the protein. The extracellular regions of the membrane protein, which will thus be exposed in the digestive tract of the flea or at other membrane locations, can be identified and peptide sequences which correspond to the amino acid sequences in these regions used as active ingredients in vaccines. These antigens, when used to immunize hosts for the flea population, raise antibodies which are capable of interfering with the digestive or other processes of the parasite when a blood meal is ingested.

The peptide fragments should be of at least 6 amino acids in length and preferably derived from those portions of the extracellular regions of the flea protein which are least homologous with the corresponding sequences in the host. The peptides can be synthesized using standard solid phase (or solution phase) synthesis techniques as is generally known in the art. If the peptides are of sufficient length, it may be more convenient to synthesize them using recombinant techniques from synthetic or isolated DNA sequences. The peptides may be prepared having a region corresponding to the above-mentioned extracellular regions as part of a "fusion" with a longer peptide sequence, or the peptide corresponding to the extracellular portion may be of sufficient length to be immunogenic by itself. In addition, the peptides can be synthesized so that the antigenic regions are present in tandem repeats, thus enhancing immunogenicity, and/or the antigenic determinants can be conjugated to carriers of neutral antigenicity such as diphtheria toxoid, KLH or a serum albumin. Standard techniques for covalently binding or otherwise associating the antigens of the invention with carriers are known in the art, and include direct techniques such as crosslinking with glutaraldehyde or reductive amination or the use of synthetic linkers such as those provided by Pierce Chemical Company, Rockford, Ill.

The immunogens containing the antigenic determinants of interest are then administered to the flea host using standard immunization techniques and protocols. The immunogens are formulated for injection using standard excipients and adjuvants as is generally known in the art and is set forth, for example, in "Remington's Pharmaceutical Sciences," latest edition, Mack Publishing Company, Easton, Pa. The dosage levels and timing of the immunization protocols are determinable by routine optimization techniques and monitoring the bloodstream of the immunized animal for elevated serum titers with respect to these antigenic determinants.

The immunized animals are then resistant to flea infestation by virtue of the antibody content of the bloodstream which will be ingested by the flea parasite as part of a blood meal. Antibodies immunoreactive with the membrane-borne binding protein then interrupt the functioning of the receptor and thus the metabolism of the parasite, neutralizing the infestation.

The following examples are intended to illustrate but not to limit the invention.

EXAMPLE 1

Cloning of Flea Sodium Pump α-Subunit

The Na+/K+ ATPase (NA+ pump) of the flea is localized in the midgut, as indicated schematically in FIG. 1. This is verified by means of Western blots. In Western blots of whole flea and flea midgut extracts (using a monoclonal against the chicken α-subunit that also recognizes the *Drosophila* pump) showed a band of about 100 kD that appeared to be enriched in the midgut extract. It was clear that the 100 kd bend representing the sodium pump is most highly concentrated in the midgut.

Primers derived from the *Drosophila* sequence were used to synthesize PCR products from first strand *Drosophila* cDNA and a flea cDNA library.

SP1: 5'-CTG GCC ACC GTA ACT GTG TGC CTG ACC CTT and (SEQ ID NO: 1)
SP3: 5'-GAC GGT CTC GTT GCC CTC GGA TAG (SEQ ID NO: 2)

These primers produced a flea product that comigrated with the corresponding *Drosophila* PCR product. Subcloning and sequence analysis of this fragment showed it to encode part of the flea Na+ pump α-subunit.

Flea cDNA clones encoding the α-subunit were isolated from a whole-body, unfed flea λgt11 library screened with a PCR fragment derived from *Drosophila* first strand cDNA using primers SP1 with SP3. First round positives were then rescreened with a flea PCR fragment that was generated using the same primers.

Flea clones were also identified using the flea PCR fragment for all rounds of screening. Hybridization conditions were as follows:

Drosophila Probe
40% formamide
5× SSPE
100 ug/ml yeast tRNA
5× Denhardt's
0.1% SDS
37° C.

Wash filters in 3× SSC at room temperature two times, then in 0.5× SSC at 50° C. for 20 min.

Flea Probe
40% formamide
5× SSPE
0.5% nonfat dry milk
0.1% SDS
42° C.

Wash filters in 3× SSC at room temperature three times, then in 0.4% SSC at 50°-60° C. for 10 min.

Approximately 10 positive plaques per 25,000 phage were obtained. Eight clones were purified. Using λgt11 primers the inserts from these 8 clones were PCR amplified. Clones #10-2 and #1-5 were the largest, having inserts of about 4 kb. Clone #10-2 was chosen for detailed analysis. Because an internal EcoRI site is present in the #10-2 insert, the clone was subcloned as 2 EcoRI fragments of about 1.5 and 2.5 kb into pGEM 3zf(+). The resulting plasmids are called pGEM 1.5 and pGEM 2.5.

Sequencing was performed using Sequenase on double-stranded templates. The Exo III-S1 protocol of Henikoff was used to generate deletions for rapid sequencing of specific regions of the flea Na+ pump. Primers designed from the obtained sequence are used to complete the sequence determination.

In an analogous manner the β-subunit is recovered. A PCR fragment corresponding to a mammalian β-subunit is generated using known sequence of β-subunit cDNAs, and this fragment is used to screen a flea library at low stringency. Sequence comparisons of the purified flea products with the vertebrate sequence verify the cloning of the flea Na+ pump β-subunit.

The relevant sequence for the α-subunit is shown as sequence ID no. 1, and in FIGS. 2A, 2B and 2C.

EXAMPLE 2

Screen for Reagents

The genes encoding α- and β-subunits of the flea Na+ pump are expressed in mammalian cell lines using standard procedures. Suitable mammalian vectors include the LK444 and pMAM vectors described above.

Standard assays for Na+ pump activity in intact cells measure the uptake of $^{86}RbCl$, which enters the cells with K+. The activity of the Na+ pump is determined by comparing total Rb+ uptake in the presence of absence of ouabain, a specific inhibitor of the Na+ pump.

Cells are grown in 24 well culture dishes. One or two days prior to uptake measurements, the cells are grown in medium supplemented with $^3H$-leucine. Determination of leucine incorporation gives a measure of cell number. Before uptake experiments, the cells are washed, then pre-incubated for 30 min in uptake buffer plus ouabain (if desired) or other chemicals. At time zero, $^{86}Rb+$ is added to the medium in each well, and after a period of time (usually 15 min) the cells are washed 4 times in ice-cold Hank's, then dissolved in NaOH-SDS. Samples are counted after addition of scintillation fluid. The ratio of $^{86}Rb+/^3H$ gives a relative measure of Na+ pump activity.

EXAMPLE 3

Peptides and Fusions for Vaccine Preparations

Figure 3:
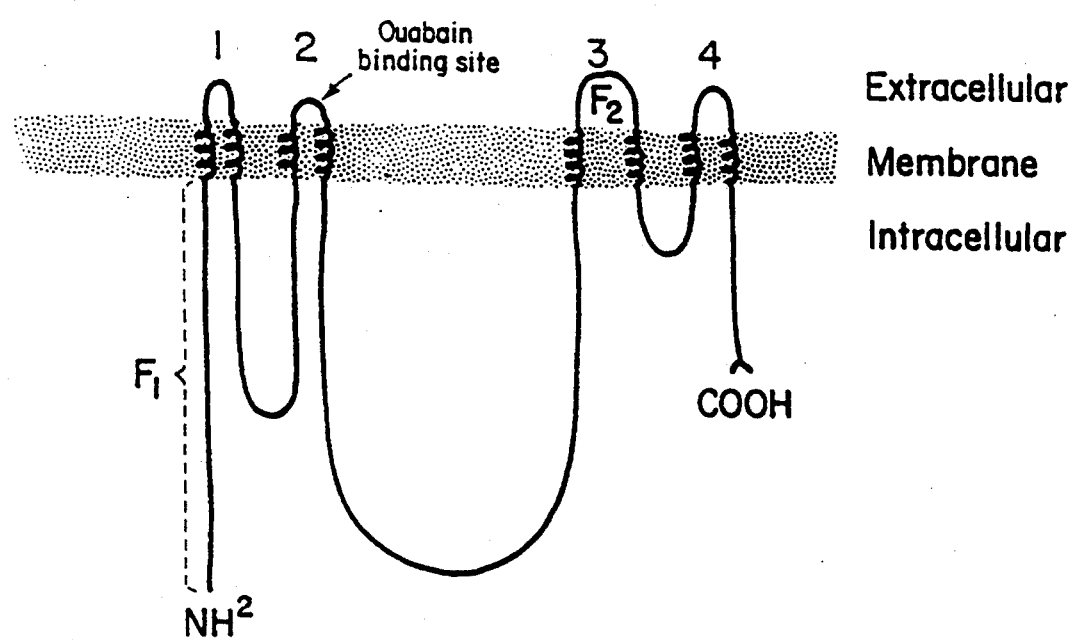
FIG. 3 is a cartoon drawing of the disposition of the flea sodium pump in the cellular membrane.

Based upon hydropathicity profiles, chemical modification studies, and homology to the $Ca^{2+}$ ATPase, eight hydrophobic regions of the Na+ pump have been suggested to be transmembrane domains. A diagram of the deduced disposition of the sodium pump in the cellular membrane is shown in FIG. 3. The extracellular regions are shown as regions 1, 2, 3 and 4, thus, four peptide regions, presumed to be external to the cell, link these domains as follows: region 1 connects hydrophobic domain 1 and 2; region 2, domains 3 and 4; region 3, domains 5 and 6; region 4, domains 7 and 8.

Peptide or fusion proteins corresponding to these extracellular regions are synthesized and used as immunogens. Fusion peptides can be prepared by ligating the DNA encoding the peptides into the expression vector pGX-3X so that when the plasmid is expressed in *E. coli* the protein encoded by the DNA insert produces a fusion protein with glutathione-S-transferase as described in detail by Smith, D. B., et al., *Gene* (1988) 67:31–40. After transforming into *E. coli*, successful transformants are grown in the presence of IPTG and the induced fusion protein is purified from the lysate by affinity chromatography with glutathione beads as described by Smith et al., (supra). The sequences of the flea Na+ pump regions are deduced from the nucleotide sequence of the flea pump cDNA and are as follows. The number of residues indicated is that corresponding to the underlined portions shown, which constitute the region external to the membrane. The additional residues lacking * are in the native sequence; the C * residues are added in synthesis for convenience in coupling.

| Region | Number of Residues | Sequence | |
|---|---|---|---|
| 1 | 12 | C*SIQASTVEEPADDNLYC* | (SEQ ID NO: 3) |
| 2 | 6 | C*ILNYHWLDAVC* | (SEQ ID NO: 4) |
| 3 | 38 | DLGTDMVPAISLAYEHAEADIMKRPPRDPVNDKLVNSR | (SEQ ID NO: 5) |
| 4 | 15 | CKTRRNSLLHQGMRNC* | (SEQ ID NO: 6) |

For region 3, peptides corresponding to the region YEHAEADIMKRPPRDPVNDKLVNSR (SEQ ID NO:7) are preferred.

---

We claim:

1. A method to identify reagents effective in controlling flea infestation which method comprises contacting a flea membrane (Na+/K+)ATPase recombinantly produced on the membrane of a first host cell with a candidate reagent, and determining the degree of binding of said candidate reagent to said first host cell; contacting a membrane (Na+/K+)ATPase from a nonflea species recombinantly produced on the membrane of a second host cell with said candidate reagent and determining the degree of binding of said candidate reagent to said second host cell; and comparing the degree of binding of the candidate reagent with said first host cell with the binding of said reagent to said second host cell;
whereby a higher degree of binding to said first host cell characterizes a successful candidate reagent.

2. The method of claim 1 wherein said flea membrane is a midgut membrane.

3. The method of claim 1 wherein the degree of binding to membrane protein is determined by degree of inhibition of labeled rubidium uptake in cells producing said membrane protein by the candidate reagent.

* * * * *

SEQUENCE LISTING ( 1 ) GENERAL INFORMATION:

( i ) APPLICANT: Yamanaka, Miles
                        Reeves, Steve
                        Dale, Beverly ( i i ) TITLE OF INVENTION: FLEA MEMBRANE BINDING SITE PROTEINS
                  AS VACCINES AND SCREENING TOOLS ( i i i ) NUMBER OF SEQUENCES: 13

( 2 ) INFORMATION FOR SEQ ID NO:1:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

CTGGCCACCG TAACTGTGTG CCTGACCCTT                                              3 0

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

GACGGTCTCG TTGCCCTCGG ATAG                                                    2 4

( 2 ) INFORMATION FOR SEQ ID NO:3:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /note="added in synthesis for
                convenience in coupling"

( i x ) FEATURE:
        ( A ) NAME/KEY: Modified-site
        ( B ) LOCATION: 18
        ( D ) OTHER INFORMATION: /note="added in synthesis for
                convenience in coupling"

( i x ) FEATURE:
        ( A ) NAME/KEY: Modified-site
        ( B ) LOCATION: 4..15
        ( D ) OTHER INFORMATION: /note="Constitutes the region
                external to the membrane"

( x i ) SEQUENCE DESCRIPTION: SEQ ID NO:3:

Cys Ser Ile Gln Ala Ser Thr Val Glu Glu Pro Ala Asp Asp Asn Leu
1               5                   10                      15

Tyr Cys ( 2 ) INFORMATION FOR SEQ ID NO:4:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /note="added in synthesis for convenience in coupling"

( i x ) FEATURE:
        ( A ) NAME/KEY: Modified-site
        ( B ) LOCATION: 12
        ( D ) OTHER INFORMATION: /note="added in synthesis for convenience in coupling"

( i x ) FEATURE:
        ( A ) NAME/KEY: Modified-site
        ( B ) LOCATION: 4..9
        ( D ) OTHER INFORMATION: /note="Constitutes the region external to the membrane"

( x i ) SEQUENCE DESCRIPTION: SEQ ID NO:4:

Cys Ile Leu Asn Tyr His Trp Leu Asp Ala Val Cys
1               5                   10

( 2 ) INFORMATION FOR SEQ ID NO:5:

( i ) SEQUENCE CHARACTERISTICS:
        ( A ) LENGTH: 38 amino acids
        ( B ) TYPE: amino acid
        ( C ) STRANDEDNESS: single
        ( D ) TOPOLOGY: linear ( i x ) FFATURE:
        ( A ) NAME/KEY: Modified-site
        ( B ) LOCATION: 1..38
        ( D ) OTHER INFORMATION: /note="Constitutes the region external to the membrane"

( x i ) SEQUENCE DESCRIPTION: SEQ ID NO:5:

Asp Leu Gly Thr Asp Met Val Pro Ala Ile Ser Leu Ala Tyr Glu His
1               5                   10                      15

Ala Glu Ala Asp Ile Met Lys Arg Pro Pro Arg Asp Pro Val Asn Asp
                20                  25                  30

Lys Leu Val Asn Ser Arg
            35

( 2 ) INFORMATION FOR SEQ ID NO:6:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 2..15
        ( D ) OTHER INFORMATION: /note="Constitutes the region external to the membrane"

( i x ) FEATURE:
        ( A ) NAME/KEY: Modified-site (B) LOCATION: 16
(D) OTHER INFORMATION: /note="Added in synthesis for
 convenience in coupling"

(x i) SEQUENCE DESCRIPTION: SEQ ID NO:6:

Cys Lys Thr Arg Arg Asn Ser Leu Leu His Gln Gly Met Arg Asn Cys
1               5                   10                  15

(2) INFORMATION FOR SEQ ID NO:7:

(i) SEQUENCE CHARACTERISTICS:
        (A) LENGTH: 25 amino acids
        (B) TYPE: amino acid
        (C) STRANDEDNESS: single
        (D) TOPOLOGY: linear (x i) SEQUENCE DESCRIPTION: SEQ ID NO:7:

Tyr Glu His Ala Glu Ala Asp Ile Met Lys Arg Pro Pro Arg Asp Pro
1               5                   10                  15

Val Asn Asp Lys Leu Val Asn Ser Arg
            20                  25

(2) INFORMATION FOR SEQ ID NO:8:

(i) SEQUENCE CHARACTERISTICS:
        (A) LENGTH: 12 amino acids
        (B) TYPE: amino acid
        (C) STRANDEDNESS: single
        (D) TOPOLOGY: linear (x i) SEQUENCE DESCRIPTION: SEQ ID NO:8:

Gln Ala Ser Thr Val Glu Glu Pro Ala Asp Asp Asn
1               5                   10

(2) INFORMATION FOR SEQ ID NO:9:

(i) SEQUENCE CHARACTERISTICS:
        (A) LENGTH: 6 amino acids
        (B) TYPE: amino acid
        (C) STRANDEDNESS: single
        (D) TOPOLOGY: linear (x i) SEQUENCE DESCRIPTION: SEQ.ID NO:9:

Asn Tyr His Trp Leu Asp
1               5

(2) INFORMATION FOR SEQ ID NO:10:

(i) SEQUENCE CHARACTERISTICS:
        (A) LENGTH: 24 amino acids
        (B) TYPE: amino acid
        (C) STRANDEDNESS: single
        (D) TOPOLOGY: linear (x i) SEQUENCE DESCRIPTION: SEQ ID NO:10:

Glu His Ala Glu Ala Asp Ile Met Lys Arg Pro Pro Arg Asp Pro Val
1               5                   10                  15

Asn Asp Lys Leu Val Asn Ser Arg
            20

(2) INFORMATION FOR SEQ ID NO:11:

(i) SEQUENCE CHARACTERISTICS:
        (A) LENGTH: 14 amino acids
        (B) TYPE: amino acid
        (C) STRANDEDNESS: single
        (D) TOPOLOGY: linear (x i) SEQUENCE DESCRIPTION: SEQ ID NO:11:

Lys Thr Arg Arg Asn Ser Leu Leu His Gln Gly Met Arg Asn
 1               5                        10

(2) INFORMATION FOR SEQ ID NO:12:

(i) SEQUENCE CHARACTERISTICS:
       (A) LENGTH: 3111 base pairs
       (B) TYPE: nucleic acid
       (C) STRANDEDNESS: single
       (D) TOPOLOGY: linear (ix) FEATURE:
       (A) NAME/KEY: CDS
       (B) LOCATION: 1..3111

(xi) SEQUENCE DESCRIPTION: SEQ ID NO:12:

| | | | | | | | | | | | | | | | | |
|---|---|---|---|---|---|---|---|---|---|---|---|---|---|---|---|---|
| ATG | GAT | GAT | AAG | CAT | GGG | CGT | TCC | GAT | TCG | TAT | CGC | GTG | GCT | ACA | GTA | 48 |
| Met | Asp | Asp | Lys | His | Gly | Arg | Ser | Asp | Ser | Tyr | Arg | Val | Ala | Thr | Val | |
| 1 | | | | 5 | | | | | 10 | | | | | 15 | | |
| CCT | ACC | ATA | GAT | GAC | AAT | TTG | ACA | GCA | GAC | GGT | CAA | TAC | AAG | TCG | CGA | 96 |
| Pro | Thr | Ile | Asp | Asp | Asn | Leu | Thr | Ala | Asp | Gly | Gln | Tyr | Lys | Ser | Arg | |
| | | | 20 | | | | | 25 | | | | | 30 | | | |
| CGT | AAA | ACG | CCA | ACG | AAA | AAG | CAA | AGG | AAG | GAA | GGA | GAG | CTT | GAT | GAC | 144 |
| Arg | Lys | Thr | Pro | Thr | Lys | Lys | Gln | Arg | Lys | Glu | Gly | Glu | Leu | Asp | Asp | |
| | | 35 | | | | | 40 | | | | | 45 | | | | |
| TTG | AAA | CAA | GAA | TTA | GAT | ATC | GAT | TTT | CAC | AAA | GTA | TCA | CCC | GAA | GAA | 192 |
| Leu | Lys | Gln | Glu | Leu | Asp | Ile | Asp | Phe | His | Lys | Val | Ser | Pro | Glu | Glu | |
| | 50 | | | | | 55 | | | | | 60 | | | | | |
| TTA | TAT | CAA | CGA | TTT | AAT | ACT | CAC | CCC | GAA | AAT | GGT | CTT | AGT | CAC | GCC | 240 |
| Leu | Tyr | Gln | Arg | Phe | Asn | Thr | His | Pro | Glu | Asn | Gly | Leu | Ser | His | Ala | |
| 65 | | | | | 70 | | | | | 75 | | | | | 80 | |
| AAG | GCG | AAA | GAA | AAC | TTA | GAA | AGA | GAT | GGA | CCG | AAT | GCT | TTG | ACC | CCG | 288 |
| Lys | Ala | Lys | Glu | Asn | Leu | Glu | Arg | Asp | Gly | Pro | Asn | Ala | Leu | Thr | Pro | |
| | | | | 85 | | | | | 90 | | | | | 95 | | |
| CCG | AAA | CAA | ACA | CCA | GAA | TGG | GTC | AAA | TTT | TGC | AAG | AAC | TTG | TTT | GGA | 336 |
| Pro | Lys | Gln | Thr | Pro | Glu | Trp | Val | Lys | Phe | Cys | Lys | Asn | Leu | Phe | Gly | |
| | | | 100 | | | | | 105 | | | | | 110 | | | |
| GGA | TTC | GCC | TTG | TTG | TTG | TGG | ATC | GGT | GCC | ATT | TTA | TGT | TTT | GTC | GCA | 384 |
| Gly | Phe | Ala | Leu | Leu | Leu | Trp | Ile | Gly | Ala | Ile | Leu | Cys | Phe | Val | Ala | |
| | | 115 | | | | | 120 | | | | | 125 | | | | |
| TAC | TCC | ATC | CAA | GCT | AGT | ACT | GTG | GAA | GAA | CCA | GCA | GAT | GAT | AAT | TTG | 432 |
| Tyr | Ser | Ile | Gln | Ala | Ser | Thr | Val | Glu | Glu | Pro | Ala | Asp | Asp | Asn | Leu | |
| | 130 | | | | | 135 | | | | | 140 | | | | | |
| TAT | CTT | GGT | ATT | GTA | TTG | GCG | GCT | GTA | GTT | ATA | GTT | ACT | GGT | ATA | TTT | 480 |
| Tyr | Leu | Gly | Ile | Val | Leu | Ala | Ala | Val | Val | Ile | Val | Thr | Gly | Ile | Phe | |
| 145 | | | | | 150 | | | | | 155 | | | | | 160 | |
| TCG | TAT | TAC | CAA | GAA | TCC | AAG | AGT | TCC | AAA | ATT | ATG | GAA | AGT | TTC | AAA | 528 |
| Ser | Tyr | Tyr | Gln | Glu | Ser | Lys | Ser | Ser | Lys | Ile | Met | Glu | Ser | Phe | Lys | |
| | | | | 165 | | | | | 170 | | | | | 175 | | |
| AAC | ATG | GTT | CCA | CAG | TTT | GCA | ACA | GTA | TTA | CGT | GAA | GGT | GAA | AAA | TTA | 576 |
| Asn | Met | Val | Pro | Gln | Phe | Ala | Thr | Val | Leu | Arg | Glu | Gly | Glu | Lys | Leu | |
| | | | 180 | | | | | 185 | | | | | 190 | | | |
| ACC | TTA | CGA | GCG | GAA | GAT | TTA | GTA | CTC | GGA | GAT | GTC | GTA | GAA | GTG | AAA | 624 |
| Thr | Leu | Arg | Ala | Glu | Asp | Leu | Val | Leu | Gly | Asp | Val | Val | Glu | Val | Lys | |
| | | 195 | | | | | 200 | | | | | 205 | | | | |
| TTC | GGC | AGC | AGG | ATA | CCT | GCA | GAT | ATC | CGT | ATT | ATT | GAA | AGC | CGA | GGA | 672 |
| Phe | Gly | Ser | Arg | Ile | Pro | Ala | Asp | Ile | Arg | Ile | Ile | Glu | Ser | Arg | Gly | |
| | 210 | | | | | 215 | | | | | 220 | | | | | |
| TTC | AAG | GTA | GAC | AAG | TCT | TCC | TTG | ACT | GGT | GAA | TCA | GAA | CCT | CAA | TCT | 720 |
| Phe | Lys | Val | Asp | Lys | Ser | Ser | Leu | Thr | Gly | Glu | Ser | Glu | Pro | Gln | Ser | |
| 225 | | | | | 230 | | | | | 235 | | | | | 240 | |
| CGA | GGT | CCC | GAG | TTT | ACA | AAT | GAA | AAG | CCT | TTA | GAA | ACG | AAG | AAC | TTG | 768 |
| Arg | Gly | Pro | Glu | Phe | Thr | Asn | Glu | Lys | Pro | Leu | Glu | Thr | Lys | Asn | Leu | |
| | | | | 245 | | | | | 250 | | | | | 255 | | |

| | | | | | | | | | | | | | | | | |
|---|---|---|---|---|---|---|---|---|---|---|---|---|---|---|---|---|
| GCG | TTC | TTC | TCT | ATC | AAC | GCC | GTC | GAA | GGT | ACT | GCC | AAA | GGT | GTC | GTT | 816 |
| Ala | Phe | Phe | Ser | Ile | Asn | Ala | Val | Glu | Gly | Thr | Ala | Lys | Gly | Val | Val | |
| | | | 260 | | | | 265 | | | | | 270 | | | | |
| ATC | AGC | TGT | GGA | GAC | AAC | ACT | GTC | ATG | GGT | CGT | ATT | GCC | GGC | TTG | GCT | 864 |
| Ile | Ser | Cys | Gly | Asp | Asn | Thr | Val | Met | Gly | Arg | Ile | Ala | Gly | Leu | Ala | |
| | | 275 | | | | | 280 | | | | | 285 | | | | |
| TCA | GGC | TTG | GAC | ACT | GGG | GAG | ACT | CCA | ATC | GCT | AAA | GAA | ATT | CAT | CAC | 912 |
| Ser | Gly | Leu | Asp | Thr | Gly | Glu | Thr | Pro | Ile | Ala | Lys | Glu | Ile | His | His | |
| 290 | | | | | 295 | | | | | | 300 | | | | | |
| TTC | ATT | CAT | CTC | ATC | ACT | GGA | GTC | GCT | GTA | TTT | TTA | GGT | GTA | ACA | TTC | 960 |
| Phe | Ile | His | Leu | Ile | Thr | Gly | Val | Ala | Val | Phe | Leu | Gly | Val | Thr | Phe | |
| 305 | | | | 310 | | | | | 315 | | | | | 320 | | |
| TTT | GTT | ATT | CGA | ATT | ATT | TTG | AAC | TAC | CAT | TGG | TTA | GAC | GCT | GTC | ATC | 1008 |
| Phe | Val | Ile | Ala | Ile | Ile | Leu | Asn | Tyr | His | Trp | Leu | Asp | Ala | Val | Ile | |
| | | | 325 | | | | | 330 | | | | | 335 | | | |
| TTC | TTG | ATT | GGT | ATC | ATC | GTC | GCT | AAT | GTC | CCT | GAA | GGT | TTA | TTG | GCT | 1056 |
| Phe | Leu | Ile | Gly | Ile | Ile | Val | Ala | Asn | Val | Pro | Glu | Gly | Leu | Leu | Ala | |
| | | | 340 | | | | | 345 | | | | | 350 | | | |
| ACT | GTA | ACC | GTA | TGT | CTA | ACC | CTT | ACT | GCT | AAG | CGT | ATG | GCA | TCC | AAG | 1104 |
| Thr | Val | Thr | Val | Cys | Leu | Thr | Leu | Thr | Ala | Lys | Arg | Met | Ala | Ser | Lys | |
| | | | 355 | | | | | 360 | | | | | 365 | | | |
| AAT | TGT | CTT | GTC | AAG | AAT | CTT | GAA | GCT | GTA | GAA | ACT | CTT | GGT | TCT | ACC | 1152 |
| Asn | Cys | Leu | Val | Lys | Asn | Leu | Glu | Ala | Val | Glu | Thr | Leu | Gly | Ser | Thr | |
| | 370 | | | | | 375 | | | | | 380 | | | | | |
| TCA | ACT | ATC | TGC | TCA | GAC | AAA | ACT | GGC | ACA | CTG | ACC | CAG | AAC | AGA | ATG | 1200 |
| Ser | Thr | Ile | Cys | Ser | Asp | Lys | Thr | Gly | Thr | Leu | Thr | Gln | Asn | Arg | Met | |
| 385 | | | | | 390 | | | | | 395 | | | | | 400 | |
| ACT | GTA | GCC | CAC | ATG | TGG | TTT | GAC | AAC | CAG | ATT | ATT | GAA | GCC | GAC | ACC | 1248 |
| Thr | Val | Ala | His | Met | Trp | Phe | Asp | Asn | Gln | Ile | Ile | Glu | Ala | Asp | Thr | |
| | | | | 405 | | | | | 410 | | | | | 415 | | |
| ACT | GAA | GAT | CAA | TCT | GGA | GTC | GTA | TAT | GAC | AGA | ACC | AGC | CCT | GGT | TTC | 1296 |
| Thr | Glu | Asp | Gln | Ser | Gly | Val | Val | Tyr | Asp | Arg | Thr | Ser | Pro | Gly | Phe | |
| | | | 420 | | | | | 425 | | | | | 430 | | | |
| AAA | GCT | TTG | GCG | CGC | ATT | GCA | ACT | TTG | TGC | AAC | AGA | GCA | GAA | TTC | AAG | 1344 |
| Lys | Ala | Leu | Ala | Arg | Ile | Ala | Thr | Leu | Cys | Asn | Arg | Ala | Glu | Phe | Lys | |
| | | | 435 | | | | | 440 | | | | | 445 | | | |
| GGA | GGT | CAG | GAA | GGT | GTA | CCC | ATC | TTG | AAA | AAA | GAA | GTC | AGT | GGT | GAT | 1392 |
| Gly | Gly | Gln | Glu | Gly | Val | Pro | Ile | Leu | Lys | Lys | Glu | Val | Ser | Gly | Asp | |
| | 450 | | | | | 455 | | | | | 460 | | | | | |
| GCA | TCT | GAA | GCT | GCT | C7T | CTC | AAA | TGT | ATG | GAA | CTG | GCT | TTA | GGA | GAT | 1440 |
| Ala | Ser | Glu | Ala | Ala | Leu | Leu | Lys | Cys | Met | Glu | Leu | Ala | Leu | Gly | Asp | |
| 465 | | | | | 470 | | | | | 475 | | | | | 480 | |
| GTT | ATG | TCT | ATT | CGA | AAA | CGA | AAT | AAG | AAA | GTC | TGT | GAA | ATT | CCA | TTT | 1488 |
| Val | Met | Ser | Ile | Arg | Lys | Arg | Asn | Lys | Lys | Val | Cys | Glu | Ile | Pro | Phe | |
| | | | | 485 | | | | | 490 | | | | | 495 | | |
| AAC | TCC | ACA | AAC | AAA | TAC | CAG | GTT | TCC | ATT | CAC | GAA | ACT | GAA | GAT | GCG | 1536 |
| Asn | Ser | Thr | Asn | Lys | Tyr | Gln | Val | Ser | Ile | His | Glu | Thr | Glu | Asp | Ala | |
| | | | 500 | | | | | 505 | | | | | 510 | | | |
| TCA | GAC | CCC | CGT | CAT | GTA | ATG | GTT | ATG | AAA | GGA | GCT | CCT | GAA | AGA | ATC | 1584 |
| Ser | Asp | Pro | Arg | His | Val | Met | Val | Met | Lys | Gly | Ala | Pro | Glu | Arg | Ile | |
| | | | 515 | | | | | 520 | | | | | 525 | | | |
| TTA | GAA | AAA | TGT | TCC | ACC | ATC | TTC | ATT | GGA | GGA | AAG | GAA | AAA | CTA | CTG | 1632 |
| Leu | Glu | Lys | Cys | Ser | Thr | Ile | Phe | Ile | Gly | Gly | Lys | Glu | Lys | Leu | Leu | |
| | 530 | | | | | 535 | | | | | 540 | | | | | |
| GAC | GAA | GAG | ATG | AAA | GAA | GCT | TTC | AAT | AAT | GCA | TAT | CTG | GAA | TTG | GGC | 1680 |
| Asp | Glu | Glu | Met | Lys | Glu | Ala | Phe | Asn | Asn | Ala | Tyr | Leu | Glu | Leu | Gly | |
| 545 | | | | | 550 | | | | | 555 | | | | | 560 | |
| GGT | CTT | GGA | GAG | CGT | GTA | TTG | GGC | TTT | TGT | GAT | CTC | ATG | TTG | CCT | ACA | 1728 |
| Gly | Leu | Gly | Glu | Arg | Val | Leu | Gly | Phe | Cys | Asp | Leu | Met | Leu | Pro | Thr | |
| | | | | 565 | | | | | 570 | | | | | 575 | | |
| GAC | AAA | TTC | CCC | TTA | GGT | TTC | AAA | TTC | GAC | AGC | GAT | GAT | CCC | AAC | TTC | 1776 |

|  |  |  |  |  |  |  |  |  |  |  |  |  |  |  |  |
|---|---|---|---|---|---|---|---|---|---|---|---|---|---|---|---|
| Asp | Lys | Phe | Pro<br>580 | Leu | Gly | Phe | Lys | Phe<br>585 | Asp | Ser | Asp | Asp<br>590 | Pro | Asn | Phe |

| | | | | | | | | | | | | | | | | |
|---|---|---|---|---|---|---|---|---|---|---|---|---|---|---|---|---|
| CCA | ATT | GAA | AAC | CTT | AGA | TTT | GTT | GGA | CTC | ATG | TCT | ATG | ATT | GAT | CCT | 1824 |
| Pro | Ile | Glu<br>595 | Asn | Leu | Arg | Phe | Val<br>600 | Gly | Leu | Met | Ser<br>605 | Met | Ile | Asp | Pro | |
| CCT | AGA | GCT | GCC | GTA | CCT | GAC | GCr | GTT | GCC | AAG | TGC | CGA | TCT | GCT | GGT | 1872 |
| Pro | Arg<br>610 | Ala | Ala | Val | Pro<br>615 | Asp | Ala | Val | Ala | Lys<br>620 | Cys | Arg | Ser | Ala | Gly | |
| ATC | AAG | GTT | ATC | ATG | GTT | ACA | GGA | GAT | CAT | CCA | ATC | ACT | GCA | AAA | GCC | 1920 |
| Ile<br>625 | Lys | Val | Ile | Met | Val<br>630 | Thr | Gly | Asp | His | Pro<br>635 | Ile | Thr | Ala | Lys | Ala<br>640 | |
| ATT | GCT | AAA | TCA | GTG | GGT | ATC | ATC | TCA | GAG | GGT | AAT | GAA | ACT | GTA | GAA | 1968 |
| Ile | Ala | Lys | Ser | Val<br>645 | Gly | Ile | Ile | Ser | Glu<br>650 | Gly | Asn | Glu | Thr | Val<br>655 | Glu | |
| GAT | ATC | GCG | CAA | AGA | TTG | AAT | ATT | CCT | GTA | TCA | GAG | GTA | AAT | CCA | CGA | 2016 |
| Asp | Ile | Ala | Gln<br>660 | Arg | Leu | Asn | Ile | Pro<br>665 | Val | Ser | Glu | Val | Asn<br>670 | Pro | Arg | |
| GAA | GCC | AAG | GCA | GCT | GTT | GTA | CAT | GGA | ACT | GAG | CTT | AGG | GAA | CTC | AAC | 2064 |
| Glu | Ala | Lys<br>675 | Ala | Ala | Val | Val | His<br>680 | Gly | Thr | Glu | Leu | Arg<br>685 | Glu | Leu | Asn | |
| TCT | GAT | CAG | CTC | GAT | GAA | ATT | CTT | AGG | TAT | CAC | ACT | GAA | ATT | GTA | TTT | 2112 |
| Ser | Asp | Gln<br>690 | Leu | Asp | Glu | Ile | Leu<br>695 | Arg | Tyr | His | Thr | Glu<br>700 | Ile | Val | Phe | |
| GCT | CGG | ACA | TCT | CCT | CAA | CAA | AAG | CTG | ATT | ATT | GIT | GAA | GGA | TGC | CAA | 2160 |
| Ala | Arg<br>705 | Thr | Ser | Pro | Gln<br>710 | Gln | Lys | Leu | Ile | Ile<br>715 | Val | Glu | Gly | Cys | Gln<br>720 | |
| CGT | ATG | GGT | GCT | ATT | GTC | GCC | GTA | ACT | GGT | GAT | GGT | GTG | AAT | GAC | TCA | 2208 |
| Arg | Met | Gly | Ala | Ile<br>725 | Val | Ala | Val | Thr | Gly<br>730 | Asp | Gly | Val | Asn | Asp<br>735 | Ser | |
| CCT | GCT | TTG | AAA | AAG | GCT | GAT | ATT | GGT | GTT | GCC | ATG | GGT | ATT | GCC | GGA | 2256 |
| Pro | Ala | Leu | Lys<br>740 | Lys | Ala | Asp | Ile | Gly<br>745 | Val | Ala | Met | Gly | Ile<br>750 | Ala | Gly | |
| TCT | GAT | GTA | TCA | AAA | CAG | GCT | GCT | GAC | ATG | ATT | TTA | TTA | GAT | GAC | AAC | 2304 |
| Ser | Asp | Val<br>755 | Ser | Lys | Gln | Ala | Ala<br>760 | Asp | Met | Ile | Leu | Leu<br>765 | Asp | Asp | Asn | |
| TTT | GCA | TCT | ATT | GTC | ACT | GGT | GTG | GAA | GAG | GGT | CGT | TTG | ATA | TTC | GAC | 2352 |
| Phe | Ala | Ser | Ile<br>770 | Val | Thr | Gly | Val<br>775 | Glu | Glu | Gly | Arg | Leu<br>780 | Ile | Phe | Aup | |
| AAT | CTG | AAG | AAA | TCT | ATT | GCT | TAC | ACA | TTG | ACT | TCA | AAT | ATC | CCA | GAA | 2400 |
| Asn | Leu<br>785 | Lys | Lys | Ser | Ile<br>790 | Ala | Tyr | Thr | Leu | Thr<br>795 | Ser | Asn | Ile | Pro | Glu<br>800 | |
| ATT | TCA | CCA | TTC | TTG | GCA | TTC | ATC | TTA | TGT | GAT | ATC | CCG | CTA | CCT | TTG | 2448 |
| Ile | Ser | Pro | Phe | Leu<br>805 | Ala | Phe | Ile | Leu | Cys<br>810 | Asp | Ile | Pro | Leu | Pro<br>815 | Leu | |
| GGA | ACT | GTA | ACA | ATC | TTG | TGC | ATT | GAC | TTG | GGA | ACT | GAC | ATG | GTG | CCT | 2496 |
| Gly | Thr | Val | Thr<br>820 | Ile | Leu | Cys | Ile | Asp<br>825 | Leu | Gly | Thr | Asp | Met<br>830 | Val | Pro | |
| GCC | ATC | TCA | TTG | GCC | TAC | GAA | CAT | GCT | GAA | GCT | GAT | ATC | ATG | AAG | AGG | 2544 |
| Ala | Ile | Ser<br>835 | Leu | Ala | Tyr | Glu | His<br>840 | Ala | Glu | Ala | Asp | Ile<br>845 | Met | Lys | Arg | |
| CCG | CCT | AGA | GAT | CCA | GTC | AAT | GAC | AAA | CTT | GTA | AAT | TCC | AGA | CTT | ATC | 2592 |
| Pro | Pro<br>850 | Arg | Asp | Pro | Val | Asn<br>855 | Asp | Lys | Leu | Val | Asn<br>860 | Ser | Arg | Leu | Ile | |
| TCT | ATG | GCT | TAT | GGG | CAA | ATC | GGA | ATG | ATT | CAA | GCA | GCT | GCT | GGA | TTC | 2640 |
| Ser | Met<br>865 | Ala | Tyr | Gly | Gln | Ile<br>870 | Gly | Met | Ile | Gln | Ala<br>875 | Ala | Ala | Gly | Phe<br>880 | |
| TTT | GTA | TAC | TTT | GTA | ATC | ATG | GCT | GAA | AAT | GGA | TTC | TTA | CCC | ATG | AAA | 2688 |
| Phe | Val | Tyr | Phe<br>885 | Val | Ile | Met | Ala | Glu<br>890 | Asn | Gly | Phe | Leu | Pro<br>895 | Met | Lys | |
| TTG | TTT | GGA | ATT | AGA | AAA | CAA | TGG | GAC | TCG | AAA | GCT | GTC | AAT | GAT | CTA | 2736 |
| Leu | Phe | Gly | Ile<br>900 | Arg | Lys | Gln | Trp | Asp<br>905 | Ser | Lys | Ala | Val | Asn<br>910 | Asp | Leu | |

| | | | | | | | | | | | | | | | | |
|---|---|---|---|---|---|---|---|---|---|---|---|---|---|---|---|---|
| ACA | GAT | TCT | TAT | GGA | CAA | GAA | TGG | ACA | TAC | AGA | GAT | CGC | AAG | ACT | CTT | 2784 |
| Thr | Asp | Ser | Tyr | Gly | Gln | Glu | Trp | Thr | Tyr | Arg | Asp | Arg | Lys | Thr | Leu | |
| | | 915 | | | | 920 | | | | | 925 | | | | | |
| GAA | TAT | ACC | TGC | CAC | ACT | GCC | TTC | TTC | GTC | TCT | ATT | GTC | GTT | GTA | CAA | 2832 |
| Glu | Tyr | Thr | Cys | His | Thr | Ala | Phe | Phe | Val | Ser | Ile | Val | Val | Val | Gln | |
| | 930 | | | | | 935 | | | | | 940 | | | | | |
| TGG | GCT | GAT | TTG | ATT | GTC | TGC | AAA | ACG | CGC | CGT | AAT | TCC | TTG | TTA | CAC | 2880 |
| Trp | Ala | Asp | Leu | Ile | Val | Cys | Lys | Thr | Arg | Arg | Asn | Ser | Leu | Leu | His | |
| 945 | | | | | 950 | | | | | 955 | | | | | 960 | |
| CAG | GGA | ATG | AGA | AAT | TGG | GCT | CTC | AAC | TTT | GGT | CTA | GTT | TTT | GAA | ACT | 2928 |
| Gln | Gly | Met | Arg | Asn | Trp | Ala | Leu | Asn | Phe | Gly | Leu | Val | Phe | Glu | Thr | |
| | | | | 965 | | | | | 970 | | | | | 975 | | |
| GCC | TTA | GCA | GCA | TTC | CTG | TCA | TAC | ACA | CCA | GGA | ATG | GAC | AAG | GGA | CTG | 2976 |
| Ala | Leu | Ala | Ala | Phe | Leu | Ser | Tyr | Thr | Pro | Gly | Met | Asp | Lys | Gly | Leu | |
| | | | 980 | | | | | 985 | | | | | 990 | | | |
| AGG | ATG | TTC | CCA | CTG | AAG | TTT | GTT | TGG | TGG | CTO | CCT | GCT | CTG | CCA | TTC | 3024 |
| Arg | Met | Phe | Pro | Leu | Lys | Phe | Val | Trp | Trp | Leu | Pro | Ala | Leu | Pro | Phe | |
| | | 995 | | | | 1000 | | | | | 1005 | | | | | |
| ATG | ATT | TCC | ATC | TTC | ATC | TAT | GAT | GAG | ACT | AGA | AGA | TTT | TAC | CTA | CGT | 3072 |
| Met | Ile | Ser | Ile | Phe | Ile | Tyr | Asp | Glu | Thr | Arg | Arg | Phe | Tyr | Leu | Arg | |
| | | 1010 | | | | 1015 | | | | | 1020 | | | | | |
| CGC | AAC | CCT | GGT | GGT | TGG | TTA | GAA | CAA | GAA | ACA | TAT | TAT | | | | 3111 |
| Arg | Asn | Pro | Gly | Gly | Trp | Leu | Glu | Gln | Glu | Thr | Tyr | Tyr | | | | |
| 1025 | | | | | 1030 | | | | | 1035 | | | | | | |

( 2 ) INFORMATION FOR SEQ ID NO:13:

( i ) SEQUENCE CHARACTERISTICS:
        ( A ) LENGTH: 1037 amino acids
        ( B ) TYPE: amino acid
        ( D ) TOPOLOGY: linear ( i i ) MOLECULE TYPE: protein ( x i ) SEQUENCE DESCRIPTION: SEQ ID NO:13:

| | | | | | | | | | | | | | | |
|---|---|---|---|---|---|---|---|---|---|---|---|---|---|---|
| Met | Asp | Asp | Lys | His | Gly | Arg | Ser | Asp | Ser | Tyr | Arg | Val | Ala | Thr | Val |
| 1 | | | | 5 | | | | | 10 | | | | | 15 |
| Pro | Thr | Ile | Asp | Asp | Asn | Leu | Thr | Ala | Asp | Gly | Gln | Tyr | Lys | Ser | Arg |
| | | | 20 | | | | | 25 | | | | | 30 | | |
| Arg | Lys | Thr | Pro | Thr | Lys | Lys | Gln | Arg | Lys | Glu | Gly | Glu | Leu | Asp | Asp |
| | | 35 | | | | | 40 | | | | | 45 | | | |
| Leu | Lys | Gln | Glu | Leu | Asp | Ile | Asp | Phe | His | Lys | Val | Ser | Pro | Glu | Glu |
| | 50 | | | | | 55 | | | | | 60 | | | | |
| Leu | Tyr | Gln | Arg | Phe | Asn | Thr | His | Pro | Glu | Asn | Gly | Leu | Ser | His | Ala |
| 65 | | | | | 70 | | | | | 75 | | | | | 80 |
| Lys | Ala | Lys | Glu | Asn | Leu | Glu | Arg | Asp | Gly | Pro | Asn | Ala | Leu | Thr | Pro |
| | | | | 85 | | | | | 90 | | | | | 95 | |
| Pro | Lys | Gln | Thr | Pro | Glu | Trp | Val | Lys | Phe | Cys | Lys | Asn | Leu | Phe | Gly |
| | | | 100 | | | | | 105 | | | | | 110 | | |
| Gly | Phe | Ala | Leu | Leu | Leu | Trp | Ile | Gly | Ala | Ile | Leu | Cys | Phe | Val | Ala |
| | | | 115 | | | | | 120 | | | | | 125 | | |
| Tyr | Ser | Ile | Gln | Ala | Ser | Thr | Val | Glu | Glu | Pro | Ala | Asp | Asp | Asn | Leu |
| | 130 | | | | | 135 | | | | | 140 | | | | |
| Tyr | Leu | Gly | Ile | Val | Leu | Ala | Ala | Val | Val | Ile | Val | Thr | Gly | Ile | Phe |
| 145 | | | | | 150 | | | | | 155 | | | | | 160 |
| Ser | Tyr | Tyr | Gln | Glu | Ser | Lys | Ser | Ser | Lys | Ile | Met | Glu | Ser | Phe | Lys |
| | | | | 165 | | | | | 170 | | | | | 175 | |
| Asn | Met | Val | Pro | Gln | Phe | Ala | Thr | Val | Leu | Arg | Glu | Gly | Glu | Lys | Leu |
| | | | 180 | | | | | 185 | | | | | 190 | | |
| Thr | Leu | Arg | Ala | Glu | Asp | Leu | Val | Leu | Gly | Asp | Val | Val | Glu | Val | Lys |

```
              195                      200                      205
Phe Gly Ser Arg Ile Pro Ala Asp Ile Arg Ile Ile Glu Ser Arg Gly
        210                  215              220
Phe Lys Val Asp Lys Ser Ser Leu Thr Gly Glu Ser Glu Pro Gln Ser
225             230                  235                      240
Arg Gly Pro Glu Phe Thr Asn Glu Lys Pro Leu Glu Thr Lys Asn Leu
                245              250                  255
Ala Phe Phe Ser Ile Asn Ala Val Glu Gly Thr Ala Lys Gly Val Val
            260                  265                  270
Ile Ser Cys Gly Asp Asn Thr Val Met Gly Arg Ile Ala Gly Leu Ala
        275                  280              285
Ser Gly Leu Asp Thr Gly Glu Thr Pro Ile Ala Lys Glu Ile His His
    290                  295              300
Phe Ile His Leu Ile Thr Gly Val Ala Val Phe Lau Gly Val Thr Phe
305             310                  315                      320
Phe Val Ile Ala Ile Ile Leu Asn Tyr His Trp Leu Asp Ala Val Ile
                325              330                  335
Phe Leu Ile Gly Ile Ile Val Ala Asn Val Pro Glu Gly Leu Leu Ala
            340                  345              350
Thr Val Thr Val Cys Leu Thr Leu Thr Ala Lys Arg Met Ala Ser Lys
        355                  360              365
Asn Cys Leu Val Lys Asn Leu Glu Ala Val Glu Thr Leu Gly Ser Thr
    370                  375              380
Ser Thr Ile Cys Ser Asp Lys Thr Gly Thr Leu Thr Gln Asn Arg Met
385             390                  395                      400
Thr Val Ala His Met Trp Phe Asp Asn Gln Ile Ile Glu Ala Asp Thr
                405              410                  415
Thr Glu Asp Gln Ser Gly Val Val Tyr Asp Arg Thr Ser Pro Gly Phe
            420                  425              430
Lys Ala Leu Ala Arg Ile Ala Thr Leu Cys Asn Arg Ala Glu Phe Lys
        435                  440              445
Gly Gly Gln Glu Gly Val Pro Ile Leu Lys Lys Glu Val Ser Gly Asp
    450                  455              460
Ala Ser Glu Ala Ala Leu Leu Lys Cys Met Glu Leu Ala Leu Gly Asp
465             470                  475                      480
Val Met Ser Ile Arg Lys Arg Asn Lys Lys Val Cys Glu Ile Pro Phe
                485              490                  495
Asn Ser Thr Asn Lys Tyr Gln Val Ser Ile His Glu Thr Glu Asp Ala
            500                  505              510
Ser Asp Pro Arg His Val Met Val Met Lys Gly Ala Pro Glu Arg Ile
        515                  520              525
Leu Glu Lys Cys Ser Thr Ile Phe Ile Gly Gly Lys Glu Lys Leu Leu
    530                  535              540
Asp Glu Glu Met Lys Glu Ala Phe Asn Asn Ala Tyr Leu Glu Leu Gly
545             550                  555                      560
Gly Leu Gly Glu Arg Val Leu Gly Phe Cys Asp Leu Met Leu Pro Thr
                565              570                  575
Asp Lys Phe Pro Leu Gly Phe Lys Phe Asp Ser Asp Pro Asn Phe
            580                  585              590
Pro Ile Glu Ann Leu Arg Phe Val Gly Leu Met Ser Met Ile Asp Pro
        595                  600              605
Pro Arg Ala Ala Val Pro Asp Ala Val Ala Lys Cys Arg Ser Ala Gly
    610                  615              620
Ile Lys Val Ile Met Val Thr Gly Asp His Pro Ile Thr Ala Lys Ala
625             630                  635                      640
```

```
Ile Ala Lys Ser Val Gly Ile Ile Ser Glu Gly Asn Glu Thr Val Glu
            645                 650                 655
Asp Ile Ala Gln Arg Leu Asn Ile Pro Val Ser Glu Val Asn Pro Arg
            660                 665                 670
Glu Ala Lys Ala Ala Val Val His Gly Thr Glu Leu Arg Glu Leu Asn
            675                 680                 685
Ser Asp Gln Leu Asp Glu Ile Leu Arg Tyr His Thr Glu Ile Val Phe
    690                 695                 700
Ala Arg Thr Ser Pro Gln Gln Lys Leu Ile Ile Val Glu Gly Cys Gln
705                 710                 715                 720
Arg Met Gly Ala Ile Val Ala Val Thr Gly Asp Gly Val Asn Asp Ser
            725                 730                 735
Pro Ala Leu Lys Lys Ala Aup Ile Gly Val Ala Met Gly Ile Ala Gly
            740                 745                 750
Ser Asp Val Ser Lys Gln Ala Ala Asp Met Ile Leu Leu Asp Asp Asn
            755                 760                 765
Phe Ala Ser Ile Val Thr Gly Val Glu Glu Gly Arg Leu Ile Phe Asp
    770                 775                 780
Asn Leu Lys Lys Ser Ile Ala Tyr Thr Leu Thr Ser Asn Ile Pro Glu
785                 790                 795                 800
Ile Ser Pro Phe Leu Ala Phe Ile Leu Cys Asp Ile Pro Leu Pro Leu
            805                 810                 815
Gly Thr Val Thr Ile Leu Cys Ile Asp Leu Gly Thr Asp Met Val Pro
            820                 825                 830
Ala Ile Ser Leu Ala Tyr Glu His Ala Glu Ala Asp Ile Met Lys Arg
            835                 840                 845
Pro Pro Arg Asp Pro Val Asn Asp Lys Leu Val Asn Ser Arg Leu Ile
    850                 855                 860
Ser Met Ala Tyr Gly Gln Ile Gly Met Ile Gln Ala Ala Ala Gly Phe
865                 870                 875                 880
Phe Val Tyr Phe Val Ile Met Ala Glu Asn Gly Phe Leu Pro Met Lys
            885                 890                 895
Leu Phe Gly Ile Arg Lys Gln Trp Asp Ser Lys Ala Val Asn Asp Leu
            900                 905                 910
Thr Asp Ser Tyr Gly Gln Glu Trp Thr Tyr Arg Asp Arg Lys Thr Leu
            915                 920                 925
Glu Tyr Thr Cys His Thr Ala Phe Phe Val Ser Ile Val Val Val Gln
    930                 935                 940
Trp Ala Asp Leu Ile Val Cys Lys Thr Arg Arg Asn Ser Leu Leu His
945                 950                 955                 960
Gln Gly Met Arg Asn Trp Ala Leu Asn Phe Gly Leu Val Phe Glu Thr
            965                 970                 975
Ala Leu Ala Ala Phe Leu Ser Tyr Thr Pro Gly Met Asp Lys Gly Iseu
            980                 985                 990
Arg Met Phe Pro Leu Lys Phe Val Trp Trp Leu Pro Ala Leu Pro Phe
            995                 1000                1005
Met Ile Ser Ile Phe Ile Tyr Asp Glu Thr Arg Arg Phe Tyr Leu Arg
    1010                1015                1020
Arg Asn Pro Gly Gly Trp Leu Glu Gln Glu Thr Tyr Tyr
1025                1030                1035
```